United States Patent
Nair et al.

(10) Patent No.: US 6,673,976 B1
(45) Date of Patent: Jan. 6, 2004

(54) PROCESS OF MAKING FLUORINATED ALCOHOLS

(75) Inventors: Haridasan K. Nair, Williamsville, NY (US); David Nalewajek, West Seneca, NY (US); Andrew Poss, Kenmore, NY (US)

(73) Assignee: Honeywell International, Inc, Morristown, NJ (US)

( * ) Notice: Subject to any disclaimer, the term of this patent is extended or adjusted under 35 U.S.C. 154(b) by 0 days.

(21) Appl. No.: 10/247,383

(22) Filed: Sep. 19, 2002

(51) Int. Cl.[7] .................. C07C 31/34; C07C 33/42; C07C 33/46
(52) U.S. Cl. .................. 568/842; 568/843; 568/812
(58) Field of Search .................. 568/842, 843, 568/812

(56) References Cited

U.S. PATENT DOCUMENTS 5,227,540 A * 7/1993 Knaup .................. 568/842

FOREIGN PATENT DOCUMENTS

JP          1147723       *  4/2002

* cited by examiner

Primary Examiner—Johann Richter
Assistant Examiner—Elvis O. Price
(74) Attorney, Agent, or Firm—Deborah M. Chess

(57) ABSTRACT

Provided are methods of producing fluorinated alcohols from non-perfluorinated fluoroolefins and methanol. Certain preferred embodiments of such methods involve advantageously reacting a non-perfluorinated fluoroolefin with methanol under ambient-pressure and/or low-temperature conditions.

19 Claims, 2 Drawing Sheets

PROCESS OF MAKING FLUORINATED ALCOHOLS

FIELD OF THE INVENTION

The present invention relates to methods of making fluorinated alcohols. More specifically, the present invention provides processes for producing fluorinated alcohols from non-perfluorinated fluoroolefins.

BACKGROUND OF THE INVENTION

Fluorinated alcohols find use in a wide variety of applications. For example, fluorinated alcohols are used as pharmaceuticals, inhalation anesthetics, herbicides, polymers, refrigerants, etchants, lubricants, heat transfer fluids, and the like. See, for example, Banks, R. E. et al "*Organofluorine Chemistry, Principles and Commercial Applications*" Plenum Press, New York and London, 1994, which is incorporated herein by reference. In particular, fluorinated butanols are desirable for use in the syntheses of pharmaceutical drug candidates and for use as solvents for photographic sensitizing dyes and in epoxidation and Diels-Alder reactions. See, for example, U.S. Pat. No. 3,756,830, issued to Polaroid Corp.; Van Vliet, M. C. A., et al., *Fluorinated alcohols: effective solvent for uncatalyzed epoxidations with aqueous hydrogen peroxide*, Synnlett, vol. 2, (2001), pp. 248–250; and Cativiela, C., et al., *Fluorinated alcohols as solvents for Diels-Alder reactions of chiral acrylates* Tetrahedron:Assymetry, 4(7), (1993), pp. 1613–18, each of which is incorporated herein by reference.

A number of processes for the preparation of fluorinated alcohols, in particular fluorinated butanols, using perfluorinated compounds as starting materials are described in the art. For example, Hazeldine et al., *J. Fluorine Chem.* 1985, 28, 291–302, incorporated herein by reference, describes the in vacuo reaction of hexafluoropropene with methanol under thermal, photochemical, and peroxide-initiated conditions to form fluorobutanols of the formula $CF_3CHFCF_2CR_1R_2OH$, wherein $R_1$ is hydrogen and $R_2$ is hydrogen, methyl, propyl or trifluoromethyl; or $R_1$ is methyl and $R_2$ is methyl or ethyl. U.S. Pat. Nos. 6,187,969 and 6,294,704, both issued to Daikin Industries and incorporated herein by reference, describe the preparation of fluoropropanols and fluorobutanols by reacting tetrafluoroethylene or hexafluoropropylene with methanol in the presence of a free radical generator and under a relatively high pressure (from about 0.2 MPa to about 1.2 MPa).

The present inventors have come to appreciate that such prior art methods for making fluorinated alcohols from perfluorinated starting materials are disadvantageous for several reasons. One disadvantage associated with the prior art methods is that such methods require subjecting a fluorinated-alcohol-forming reaction mixture to either very high pressure or very low pressure (e.g. under vacuum in sealed quartz vessels), making the reaction difficult and/or expensive to scale-up for industrial use. In order to create high pressure or vacuum, the reactions of the prior art methods must be conducted in sealed reactors, such as autoclaves, capable or maintaining high or low pressures without leaking. As the prior art reactions are scaled up, larger sealed reactors capable of creating and withstanding high or low pressure become necessary. Providing such large scale reactors which overcome the inherent problems of avoiding leaks on such large scale equipment tends to be highly expensive as compared to large scale vessels which need not be sealed.

The prior art methods are also disadvantageous in that many of such methods require heating reaction mixtures containing peroxides. Because peroxides tend to be explosive at elevated temperatures, the heated peroxide-containing reactions of the prior art tend to be highly, if not prohibitively, dangerous to conduct, especially on larger commercial scales.

Yet another disadvantage associated with prior art methods is the relatively long reaction times required in such methods.

Recognizing these and other drawbacks of the prior art, the present inventors have perceived a need for a new, efficient and more desirable method for producing a wide range of fluorinated alcohols. These and other objects are achieved by the present invention as described below.

DESCRIPTION OF PREFERRED EMBODIMENTS

Figure 1:
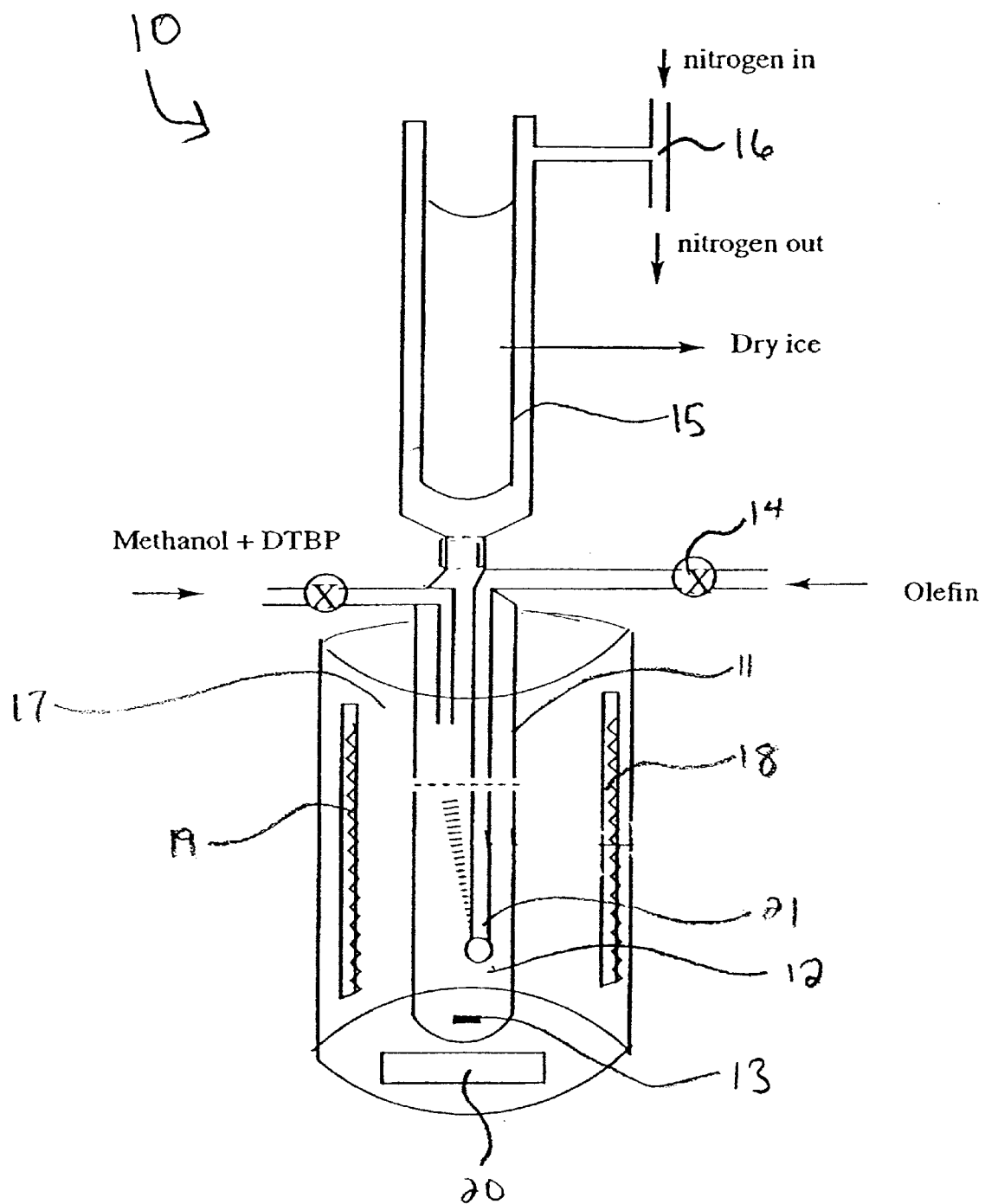
FIG. 1 shows an open system suitable for use according to certain preferred embodiments of the present invention.

The present invention is directed to methods of producing a wide range of fluorinated alcohols which overcome the disadvantages associated with prior art methods. An important aspect of the invention is the discovery that fluorinated alcohols, especially certain known and novel fluorobutanols, can be advantageously produced using non-perfluorinated fluoroolefins as a principal reagent. As used herein, the term "non-perfluorinated fluoroolefin" refers generally to any unsaturated compound, preferably having at least one double bond, at least one fluorine atom substituent, and at least one non-fluorine atom substituent. Examples of certain preferred non-perfluorinated fluoroolefins include hydrofluoroolefins. A hydrofluoroolefin, for purposes of the present invention, is an unsaturated compound, preferably having at least one double bond, at least one fluorine atom substitutent, and at least one hydrogen atom. A hydrofluoroolefin may further comprise other substituents, including non-fluorine halogens, such as chlorine, bromine and the like. Examples of preferred hydrofloroolefins include compounds described by Formula I, below:

$$CF_3CX=CYZ \qquad (I)$$

wherein X, Y and Z are independently hydrogen or halogen, provided that at least one of X, Y or Z is hydrogen.

Applicants have discovered that non-perfluorinated fluoroolefins exhibit a relatively high reactivity with alcohols under a wide range of reaction conditions to produce fluorinated alcohols. In particular, applicants have discovered that non-perfluorinated fluoroolefins can be used with great advantage in a process which comprises converting a non-perfluorinated fluoroolefin, and preferably a hydrofluoroolefin of Formula I, to a fluorinated alcohol under a pressure of from less than about 1 to about 2 atm. In certain preferred embodiments, the reaction pressures for use in the present invention include pressures of from about 1 to about 2 atm, and even more preferably from about 1 atm to about 1.5 atm. In certain more preferred embodiments, the reactions of the present invention are conducted under ambient pressure conditions. While prior art methods require the use of relatively high or low pressures to convert perfluoroolefins to fluorinated alcohols, applicants have discovered that non-perfluorinated fluoroolefins, and particularly hydrofluoroolefins, exhibit sufficient reactivity with methanol under ambient pressure conditions to effectively and efficiently produce fluorinated alcohols. Because the preferred reactions of the present invention are conducted at about ambient pressure, and thus do not require subjecting a reaction mixture to very high or very low pressures, the presently claimed methods can be readily scaled up at lower cost and without needing to address the problems associated with providing large-scale sealed reactors and problems associated with recycling methanol in such systems.

The applicants have also discovered that certain preferred methods of the present invention allow for much safer production of fluorinated alcohols via low-temperature reactions involving peroxide catalysts. The term "low-temperature", as used herein, refers generally to a reaction conducted, at least in substantial part, at a temperature of about 80° C. or less. In certain preferred embodiments, the invention provides for the reaction to be conducted, at least in substantial part, at a temperature of about 50° C. or less. In more preferred embodiments, low-temperature reactions are conducted, at least in substantial part, at a temperature of from about 15° C. to about 40° C. Applicants have discovered that non-perfluorinated fluoroolefins exhibit the ability to efficiently react with methanol, in the presence of an initiator, preferably a peroxide initiator, to form fluorinated alcohols at relatively low temperatures. Because the peroxide-initiated reactions of the claimed invention may be conducted at relatively low temperatures, there is less likelihood of unsafe reaction as compared to higher temperature prior art methods. Accordingly, the methods of the present invention are more readily and more safely scalable for commercial use.

According to certain preferred embodiments, the present invention provides methods of producing fluorinated alcohols comprising reacting a hydrofluoroolefin with methanol under conditions effective to form a fluorinated alcohol. Although applicants do not wish to be bound by or to any particular theory of operation, it is believed that the methods according to the preferred aspects of the present invention involve the reaction of a compound of Formula I with methanol as shown below.

(I)

In certain embodiments, the reacting step of the present method comprises combining a non-perfluorinated fluoroolefin with methanol to provide a reaction mixture comprising the non-perfluorinated fluoroolefin and methanol. Any of a wide range of non-perfluorinated fluoroolefins as defined above can be used according to the present invention. In certain preferred embodiments, the non-perfluorinated fluoroolefins for use in the present invention include perhalogenated non-perfluorinated fluoroolefins such as $CF_3C(Br)=CF_2$ and the like. In certain other preferred embodiments, the non-perfluorinated fluoroolefins for use in the present invention include hydrofluoroolefins, including compounds described by Formula I, such as, for example, $CF_3CH=CF_2$ (HFC-1225), $CF_3CH=CFH$ (HFC-1234zc), $CF_3CH=CH_2$ (HFC-1234zf), $CF_3CH=CHCl$ (HCFC-1233), including all cis and trans isomers thereof, mixtures of two or more thereof, and the like. In certain particularly preferred embodiments, the hydrofluoroolefin is $CF_3CH=CF_2$ (HFC-1225), $CF_3CH=CFH$ (HFC-1234zc), $CF_3CH=CH_2$ (HFC- 1234zf), or mixtures of two or more thereof.

A variety of non-perfluorinated fluoroolefins suitable for use in the present invention are commercially available, including, for example, HFC-1225 and HFC-1234zf available from Aldrich Chemical Co. or Synquest Laboratories. Furthermore, many suitable fluoroolefins are known in the literature and are obtainable by art-recognized procedures, for example, HFC-1225 and HFC-1234zc are obtainable via conventional dehydrohalogenation of HCFC-235fa and HFC-245fa, respectively (HCFC-235fa and HFC-245fa are available commercially from Honeywell International, Inc).

Methanol suitable for use in the present invention is available from any of a wide number of commercial sources. Preferably, the methanol used in the present invention is substantially anhydrous methanol. Anhydrous methanol is preferred because the presence of water in the reaction tends to hinder the formation of fluorinated alcohols. The term "substantially anhydrous", as used herein, means that the methanol contains less than about 0.05 weight percent water. In preferred embodiments, the methanol contains less than about 0.02 weight percent water.

Non-perfluorinated fluoroolefins and methanol can be combined to form a reaction mixture according to the present invention using any of a wide range of known methods and reaction conditions. For example, non-perfluorinated fluoroolefins which tend to be in the liquid state at about room temperature, or under the conditions of the reactions according to the present invention, may be directly introduced to a reaction vessel containing methanol (via any of a number of conventional methods), or may be introduced to a reaction vessel into which methanol is subsequently added. Examples of methods for combining gaseous non-perfluorinated fluoroolefins with methanol according to the present invention include bubbling the non-perfluorinated fluoroolefin into a reaction mixture comprising methanol, for example via a gas sparger, or condensing the non-perfluorinated fluoroolefin and subsequently introducing the condensed non-perfluorinated fluoroolefin into a reaction mixture comprising methanol. In embodiments wherein a gaseous non-perfluorinated fluoroolefin is condensed and then combined with methanol, the non-perfluorinated fluoroolefin may be condensed outside of a reaction vessel containing methanol and subseqently introduced to the vessel, or the gaseous non-perfluorinated fluoroolefin may be condensed inside the reaction vessel, for example, onto a cold (−78° C.) finger. In certain preferred embodiments, the present methods comprise introducing a gaseous non-perfluorinated fluoroolefin into a reaction vessel equipped with a condenser, wherein the gaseous non-perfluorinated fluoroolefin is condensed by the condenser, and combining the condensed non-perfluorinated fluoroolefin with methanol.

Those skilled in the art will appreciate that the amounts of non-perfluorinated fluoroolefin and methanol reagents to be used according to the present invention will depend on many variables, including the particular non-perfluorinated fluoroolefin being used and the desired yield from the reaction. Preferably, the amount of reagents used is an amount effective to achieve a greater than about 20% conversion, preferably greater than 40%, and even more preferably greater than about 60% by weight of the non-perfluorinated fluoroolefin starting material to a fluorinated alcohol. In certain preferred embodiments, the methanol used in the reaction mixtures of the present invention acts as both a reagent and a solvent for the fluorinated alcohol-forming reaction. Accordingly, in such embodiments, the methanol is preferably present in excess based on the molar amount of non-perfluorinated fluoroolefin used. For example, in certain preferred processes in which the non-perfluorinated fluoroolefin is HFC-1225, the mole ratio of methanol to HFC-1225 is preferably at least about 2:1, more preferably at least about 3:1, and even more preferably at least about 5:1. In certain especially preferred embodiments, the mole ratio of methanol to non-perfluorinated fluoroolefin is at least about 7:1 or greater.

Although applicants do not wish to be bound by or to any theory of operation, it is believed that, in many embodiments, the formation of a fluorinated alcohol from a non-perfluorinated fluoroolefin according to the present invention involves a free-radical process. Accordingly, in many preferred embodiments, the reaction step involves the use of a radical initiator compound. As used herein the term "radical initiator compound" refers generally to any compound, or combination of compounds, which facilitates the free radical reaction of non-perfluorinated fluoroolefins with methanol to form fluorinated alcohols. Any of a wide range of suitable radical initiator compounds can be used according to the present invention. Examples of suitable radical initiator compounds include organic peroxides, such as, dialkyl peroxides, including di-tert-butylperoxide, hydroperoxides, diacyl peroxides, peroxydicarbonates, and the like; azo compounds, such as, azo-bis-isobutyronitrile (AIBN), and the like; and combinations of two or more thereof. In certain preferred embodiments, the radical initiator compounds for use in the present invention comprise dialkyl peroxides, such as di-tert-butylperoxide.

A variety of radical initiator compounds suitable for use in the present invention are commercially available, including, for example, di-tert-butylperoxide (available under the tradename "perbutyl D" from NOF Corp, Aldrich Corp., and/or Akzo Corp.). Furthermore, many suitable radical initiator compounds are known in the literature and are obtainable by art-recognized procedures.

Any suitable amount of radical initiator compound can be used in the methods of the present invention. In certain preferred embodiments, the concentration of the radical initiator is less than about 5 mol% based on the moles of methanol in the reaction mixture. In more preferred embodiments, the concentration is from about 1 to about 3 mol%.

According to certain preferred embodiments, the reactions of the present invention comprise exposing a reaction mixture comprising a non-perfluorinated fluoroolefin, methanol, and, optionally, a radical initiator compound, to ultraviolet ("UV") irradiation. It is well-known in the art to use UV light to promote free-radical processes and those of skill in the art will be readily able to adapt conventional methods of UV irradiation to the present invention without undue experimentation. For example, in preferred embodiments, a provided mixture of the present invention is irradiated using a UV lamp at a wavelength of from about 200 to about 400 nanometers. Examples of suitable UV lamps include a Rayonet Photochemical Reactor or a photochemical reactor with mercury vapor lamp (such as those available from Ace Glass Co.).

The fluorinated-alcohol-forming reactions according to the present invention may be conducted in open reaction systems, i.e. systems open to the atmosphere or inert gas purge (wherein such systems may be equipped with a condenser to prevent the loss of volatiles), or may be conducted in closed reaction vessels. In preferred embodiments, the reactions of the present invention are conducted in open reactions systems. The open reaction systems may comprise any apparatus or combination of apparatus suitable for use in conducting a reaction according to the present invention. By way of example, FIG. 1 shows an open system 10 suitable for use according to certain preferred embodiments of the present invention. System 10 comprises a quartz reaction vessel 11 containing the reaction mixture 12 and a magnetic stir bar 13. Vessel 11 has a gas inlet valve 14 and is fitted with a dry ice condenser 15 through which the system is open to nitrogen purge 16. Vessel 11 is housed in a UV reactor 17 which contains UV lamps 18, 19 and a magnetic stirrer/fan assembly 20. Via this set-up, system 10 allows for the addition of gaseous reagent, for example a gaseous non-perfluorinated fluoroolefin, through inlet 14 which may be bubbled into mixture 12 via a gas sparger 21 and/or condensed by condenser 15 into reaction mixture 12. During or after addition of the condensed reagent, the reaction mixture may be subjected to UV irradiation from the UV lamps on the UV reactor. In light of the disclosure herein, those of skill in the art will be readily able to select open or closed systems for use in the present invention without undue experimentation.

In preferred embodiments, the present reactions are conducted under an inert gas purge. Any suitable inert gas may be used according to the present invention. Preferred inert gasses include, for example, nitrogen or argon.

Those skilled in the art will appreciate that the conditions under which the present reaction occurs, including the pressure, temperature and period of reaction, will depend on numerous factors, including the particular starting reagents used and the desired reaction yield. While the reactions of the present invention may be conducted under any suitable pressure conditions, as noted above, in preferred embodiments, the present reactions are conducted under ambient-pressure conditions. Additionally, the reactions of the present invention may be conducted at any suitable reaction temperature. In preferred embodiments, the reaction is conducted under low-temperature conditions as described above. For example, in preferred embodiments wherein the present invention comprises reacting HFC-1225 with anhydrous methanol in the presence of di-tertiarybutylperoxide, the pressure within the reaction vessel is preferably from about 1 to about 2 atm, and more preferably from about 1 to about 1.25 atm. For such embodiments, the reaction temperature is preferably from about 50° C. or less, more preferably from about 40° C. or less, and even more preferably from about 15° C. to about 40° C. The reactions of the present invention may be conducted for any suitable length of time. In certain preferred embodiments, the reaction time is preferably about 6 hours or less, and more preferably about 5 hours or less.

Any residual peroxide remaining in the reaction mixture after completion of the reaction can be removed using any of a wide range of known methods. For example, residual peroxide may be removed by washing the reaction mixture with a 10–20% aqueous sodium sulphate or sodium bisulphate solution.

Figure 2:
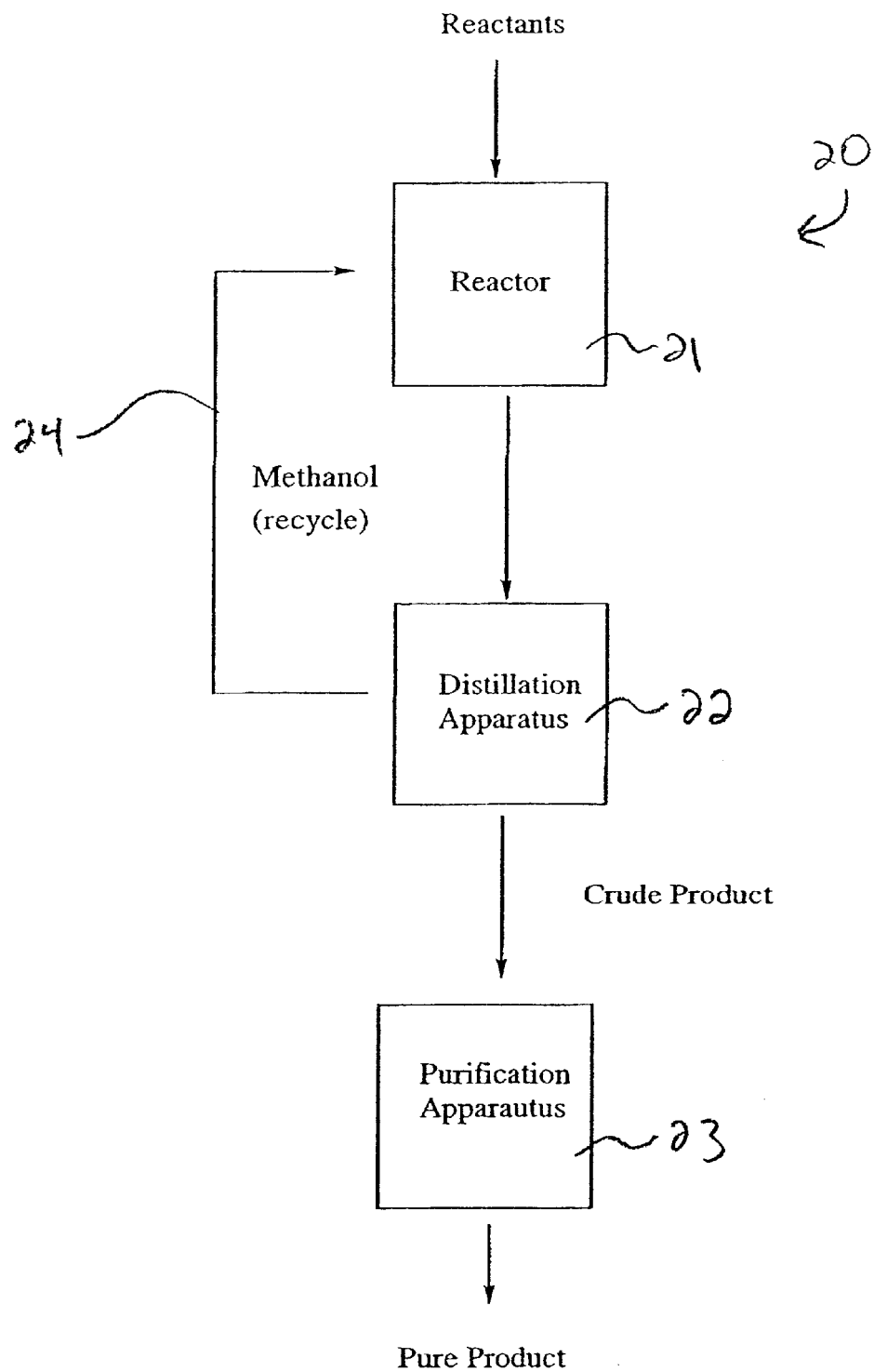
FIG. 2 is a diagram of a process according to certain preferred embodiments of the present invention.

The product formed from the reaction of the present invention may be purified by conventional methods such as: filtering, washing, drying, concentrating under reduced pressure, distillation and the like. In certain preferred embodiments, the product is purified, at least in part, via distillation. In such preferred embodiments, any methanol which is removed during distillation may be recycled back to the reaction mixture. FIG. 2 is a process diagram 20 showing such distillation and recycling steps according to certain preferred embodiments of the present invention. The reaction of the present invention is conducted in reactor 21. The reaction mixture is distilled in the distillation apparatus 22. Distilled fluorinated alcohol product is separated from the reaction mixture via apparatus 22 and purified using purification apparatus 23. Any methanol separated via distillation is recycled back to reactor 21 via recycle stream 24.

EXAMPLES

Example 1

This Example illustrates the small scale (about 7 g) preparation of 2,2,4,4,4-pentafluorobutan-1-ol ($CF_3CH_2CF_2CH_2OH$).

Under nitrogen, into a quartz tube equipped with a dry-ice condenser was added anhydrous methanol (20 g, 0.62 mol) and di-tertiarybutylperoxide (.79 g, 0.003 mol). The quartz tube was placed in a Rayonet UV photochemical reactor and HFC 1225, $CF_3CH=CF_2$ (7 g, 0.05 mol) was added drop-wise via a dry-ice condenser (−78° C.) over a period of ~30 minutes while being irradiated at 254 nm. After complete addition, the reaction mixture was irradiated for ~30 minutes. The reaction mixture was concentrated under reduced pressure. The residue was extracted in diethyl ether (~50 mL), washed with 20 mL aq. $Na_2SO_3$ (20%) and brine (10 mL). The ether layer was then concentrated to afford 7 g of the crude material which was distilled under reduced pressure (24–28 mm Hg) to afford $CF_3CH_2CF_2CH_2OH$ (4.6 g, mol) as a colorless liquid. Yield=52% based on HFC 1225. Boiling point, 62° C./24–28 mm Hg. GC-MS: m/e 164 ($C_4H_5F_5O$) for $M^+$; $^{19}F$ and $^1H$ NMR spectra are consistent with the structure. $^{19}F$ NMR ($CDCl_3$)δ=−62.4 (3F, tt overlaps), −106.5 (2F, m) ppm; $^1H$ NMR ($CDCl_3$)δ=2.7 (1H, t), 2.9 (2H, m), 3.8 (2H, m) ppm.

Example 2

This Example illustrates the preparation of 2,2,4,4,4-pentafluorobutan-1-ol ($CF_3CH_2CF_2CH_2OH$) on a larger (about 58 g) scale.

Under nitrogen, into a quartz reactor equipped with a dry-ice condenser was added anhydrous methanol (100 g, 3.10 mol) and di-tertiarybutylperoxide (3.95 g, 0.015 mol). The quartz reactor tube was placed in a Rayonet UV photochemical reactor and HFC 1225, $CF_3CH=CF_2$ (57.9 g, 0.438 mol) was added drop-wise via a dry-ice condenser (−78° C.) over a period of ~5 hours while being irradiated at 254 nm. After complete addition, the reaction mixture was irradiated for additional hour. Then the reaction mixture was concentrated under reduced pressure, the residue (~65 g) was mixed well with 120 mL aq. $Na_2SO_3$ (20%), separated the lower layer, and washed with brine (40 mL). The crude product was then distilled under reduced pressure (24–28 mm Hg) to afford 55 g $CF_3CH_2CF_2CH_2OH$ (yield 77% based on HFC 1225).

Example 3

This Example illustrates the preparation of 2,4,4,4-tetrafluorobutanol ($CF_3CH_2CFHCH_2OH$)

Under nitrogen, into a quartz tube equipped with a dry-ice condenser was added anhydrous methanol (20 g, 0.62 mol) and di-tertiarybutylperoxide (.79 g, 0.003 mol). The quartz tube was placed in a Rayonet UV photochemical reactor and HFC 1234zc, $CF_3CH=CFH$ (5 g, 0.044 mol) was added drop-wise via a dry-ice condenser (−78° C.) over a period of ~1 hour while being irradiated at (UV wavelength) 254 nm. After complete addition, the reaction mixture was irradiated for ~1 hour. The reaction mixture was concentrated under reduced pressure. The residue was extracted in diethyl ether (~50 mL), washed with 20 mL aq. $Na_2SO_3$ (20%) and brine (10 mL). The ether layer was then concentrated to afford 7 g of the crude material. Distillation of this material under reduced pressure (24–28 mm Hg) afforded $CF_3CH_2CFHCH_2OH$ (2.7g) as a colorless liquid; yield=42% based on HFC 1234 zc. Boiling point, 58° C./24 mm Hg. GC-MS: m/e at 146 ($C_4H_6F_4O$) for $M^+$; $^{19}F$ and $^1H$ NMR spectra are consistent with the structure. $^{19}F$ NMR ($CDCl_3$) δ=−64.6 (3F, m), −191.2 (1F, m) ppm; $^1H$ NMR ($CDCl_3$) δ=2.2 (1H, br), 2.4(1H, m), 2.6 (1H, m), 3.7–3.9 (2H, m), 4.9 (1H, dm) ppm.

Example 4

This Example illustrates the preparation of 3-bromo-2,2,4,4,4-pentafluorobutano-1-ol ($CF_3CHBrCF_2CH_2OH$).

In a quartz photochemical reaction vessel equipped with a dry ice condenser, a stirred mixture of methanol (20 g), ditert-butyl peroxide (0.79) and $CF_3C(Br)=CF_2$ (10 g, 0.05 mol), was irradiated at 254 nm for ~6 hr at ambient temperature for under nitrogen. (Note: $CF_3CBr=CF_2$ was added as a liquid (BP, 24–25° C.) in one lot before the reaction). Then the reaction mixture was concentrated to remove excess methanol. The concentrated material was taken in ~40 mL ether, washed with 20 ml 20% aqueous sodium bisulphite followed by brine (10 mL) and distilled to afford the $CF_3CHBrCF_2CH_2OH$ (2.0 g) as a colorless liquid. Yield=26% based on $CF_3CBr=CF_2$. Boiling point, 30–31° C./ 8–10 mm Hg. GC-MS: m/e at ($C_4H_4BrF_5O$) for $M^+$; NMR spectra are consistent with the structure.

Example 5

This Example illustrates the preparation of 2-chloro-4,4,4-trifluorobutan-1-ol ($CF_3CH_2CHClCH_2OH$).

By following the procedure outlined in Example 3, except that an equivalent amount of $CF_3CH=CHCl$ (HCFC 1233) was substituted for $CF_3CBr=CF_2$, the compound 2-chloro-4,4,4-trifluorobutan-1-ol, $CF_3CH_2CHClCH_2OH$, was prepared. Yield=20%, Bp 25–26° C./10 mm Hg. GC-MS: m/e 162 $M^+$ for ($C_4H_7F_3ClO$).

Example 6

This Example illustrates the preparation of 4,4,4-trifluorobutan-1-ol ($CF_3CH_2CH_2CH_2OH$).

By following the procedure outlined in Example 1, except that an equivalent amount of trifluoropropene $CF_3CH=CH_2$ (FC-1234 zf)) was substituted for $CF_3CH=CF_2$, the compound 4,4,4-trifluorobutan-1-ol, $CF_3CH_2CH_2CH_2OH$, was prepared. Yield=~10%. The identity of the product was confirmed with an authentic sample obtained commercially.

What is claimed is:

1. A method of producing a fluorinated alcohol comprising: providing a reaction mixture comprising a non-perfluorinated fluoroolefin, methanol, and a radical initiator; and exposing said reaction mixture to UV irradiation under conditions effective to produce a fluorinated alcohol.

2. The method of claim 1 wherein said conditions comprise exposing said reaction mixture to UV irradiation at a temperature of about 50° C. or less and at a pressure of from about 1 atm to about 2 atm.

3. The method of claim 2 wherein said non-perfluorinated fluoroolefin is a hydrofluorocarbon.

4. The method of claim 3 wherein the exposing step is conducted under ambient pressure conditions.

5. The method of claim 3 wherein the exposing step is conducted at a temperature of less than about 40° C.

6. The method of claim 3 wherein said hydrofluoroolefin is described by the formula I:

$$CF_3CX=CYZ \quad (I)$$

wherein X, Y and Z are independently hydrogen or halogen, provided that at least one of X, Y or Z is hydrogen.

7. The method of claim 1 wherein said non-perfluorinated fluoroolefin is selected from the group consisting of $CF_3CH=CF_2$, $CF_3CH=CFH$, $CF_3CH=CH_2$, $CF_3CH=CHCl$, $CF_3C(Br)=CF_2$, and mixtures of two or more thereof.

8. The method of claim 7 wherein said non-perfluorinated fluoroolefin is $CF_3CH=CF_2$.

9. The method of claim 7 wherein said non-perfluorinated fluoroolefin is $CF_3CH=CFH$.

10. The method of claim 7 wherein said non-perfluorinated fluoroolefin is $CF_3C(Br)=CF_2$.

11. The method of claim 1 wherein said radical initiator comprises an organic peroxide.

12. The method of claim 11 wherein said organic peroxide is a dialkyl peroxide.

13. The method of claim 12 wherein said dialkyl peroxide is di-tert-butylperoxide.

14. The method of claim 1 wherein said fluorinated alcohol is selected from the group consisting of $CF_3CH_2CF_2CH_2OH$, $CF_3CH_2CFHCH_2OH$, $CF_3CHBrCF_2CH_2OH$, $CF_3CH_2CHClCH_2OH$, $CF_3CH_2CH_2CH_2OH$ and mixtures of two or more thereof.

15. A method of producing a fluorinated alcohol comprising providing a reaction mixture comprising methanol, a radical initiator, and a non-perfluorinated fluoroolefin selected from the group consisting of $CF_3CH=CF_2$, $CF_3CH=CH_2$, $CF_3C(Br)=CF_2$, and mixtures of two or more thereof; and exposing said reaction mixture to UV irradiation to form a fluorinated alcohol, said reaction mixture being maintained under conditions comprising a pressure of from about 1 to about 1.5 atm and a temperature of about 80° C. or less during said exposing step.

16. The method of claim 15 wherein said reaction mixture is maintained at a temperature of about 50° C. or less during said exposing step.

17. The method of claim 16 wherein said radical initiator comprises a dialkyl peroxide.

18. The method of claim 17 wherein said dialkyl peroxide comprises di-tert-butylperoxide.

19. The method of claim 15 wherein said fluorinated alcohol is selected from the group consisting of $CF_3CH_2CF_2CH_2OH$, $CF_3CH_2CFHCH_2OH$, and mixtures of two or more thereof.

* * * * *